United States Patent

Wadle et al.

[11] Patent Number: 5,817,254
[45] Date of Patent: Oct. 6, 1998

[54] FREE-FLOWING EMULSION CONCENTRATE

[75] Inventors: Armin Wadle, Hilden; Achim Ansmann, Erkrath; Guido Baumoeller, Duesseldorf; Holger Tesmann, Juechen, all of Germany

[73] Assignee: Henkel Kommanditgesellschaft auf Aktien, Duesseldorf, Germany

[21] Appl. No.: 628,667

[22] PCT Filed: Oct. 5, 1994

[86] PCT No.: PCT/EP94/03293

§ 371 Date: May 14, 1996

§ 102(e) Date: May 14, 1996

[87] PCT Pub. No.: WO95/10259

PCT Pub. Date: Apr. 20, 1995

[30] Foreign Application Priority Data

Oct. 14, 1993 [DE] Germany .......................... 43 35 045.3

[51] Int. Cl.$^6$ ...................................................... B01J 13/00
[52] U.S. Cl. ........................ 252/312; 252/314; 514/938; 514/941
[58] Field of Search ................................... 252/312, 314; 514/938, 941

[56] References Cited

U.S. PATENT DOCUMENTS

| | | | |
|---|---|---|---|
| 4,798,682 | 1/1989 | Ansmann | 252/312 |
| 4,883,604 | 11/1989 | Veitenhansi et al. | 252/8.81 |
| 4,996,004 | 2/1991 | Bucheler et al. | 252/314 |
| 5,139,786 | 8/1992 | Ferrini et al. | 424/449 |
| 5,145,603 | 9/1992 | Paasch et al. | 252/311 |
| 5,444,041 | 8/1995 | Owen et al. | 514/2 |
| 5,494,938 | 2/1996 | Kawa et al. | 514/786 |

FOREIGN PATENT DOCUMENTS

| | | |
|---|---|---|
| 2305087 | 8/1974 | Germany . |
| 3521713 | 12/1986 | Germany . |
| 3819193 | 12/1989 | Germany . |
| 4010393 | 10/1991 | Germany . |
| WO 9207543 | 5/1992 | WIPO . |
| WO 9311865 | 6/1993 | WIPO . |

OTHER PUBLICATIONS

Database WPAT, Week 7433, London: Derwent Publications Ltd., AN–74–58602V/33, class D21, DE 2305087–A (Henkel & Cie GmbH), Abstract.

*Primary Examiner*—Richard D. Lovering
*Assistant Examiner*—Daniel S. Metzmaier
*Attorney, Agent, or Firm*—W. C. Jaeschke; J. Daniel Wood; Henry E. Millson, Jr.

[57] ABSTRACT

An aqueous emulsion concentrate comprising:
  A) a water-insoluble oil component;
  B) at least one hydrophilic nonionic emulsifier;
  C) at least one lipophilic co-emulsifier; and
  D) from about 50 to about 70% by weight of water, based on the weight of the concentrate;

wherein components A), B) and C) are present in a ratio by weight of A:B:C of 1:(0.31–1.5):(0.31–1.5); and wherein the emulsion concentrate is flowable and pumpable at 20° C.

3 Claims, No Drawings

FREE-FLOWING EMULSION CONCENTRATE

This application is filed under 35 U.S.C. § 371 and is based on PCT/EP94/03293, filed Oct. 5, 1994.

BACKGROUND OF THE INVENTION

1. Field of the Invention

This invention relates to an emulsion concentrate which is flowable and pumpable at normal temperature, to its use for the production of oil-in-water emulsions and to a process for the production of oil-in-water emulsions using the emulsion concentrate.

2. Statement of Related Art

The production of emulsion-like formulations normally involves considerable outlay on equipment because the disperse phase has to be liquefied by heating and dispersed in the continuous phase by application of shear forces. Various attempts have already been made to produce emulsion concentrates which can be diluted with the continuous phase in the absence of heat and shear forces.

For example, DE 23 05 087 C2 describes a self-emulsifying oil which can be spontaneously converted into an emulsion without heating by addition of water. One disadvantage of this self-emulsifying oil is that the emulsions produced with it are not particularly fine and, accordingly, are not stable in storage. Nor do they allow other oil components or relatively high-melting waxes to be incorporated during production of the emulsion.

DESCRIPTION OF THE INVENTION

Accordingly, the problem addressed by the present invention was to develop emulsion concentrates which would be flowable and pumpable at normal temperature and which could be further processed to emulsion-like preparations using water and oil components and optionally other additives without any need to apply heat and with only gentle stirring.

It has now surprisingly been found that this problem is solved by highly concentrated emulsions which contain hydrophilic emulsifiers and lipophilic co-emulsifiers in defined quantity ratios.

Accordingly, the present invention relates to an emulsion concentrate which is flowable and pumpable at 20° C. and which contains water-insoluble oil components (A), hydrophilic nonionic emulsifiers (B), lipophilic co-emulsifiers (C) and water, characterized in that the water content is from 50 to 70% by weight, based on the concentrate, and components (A), (B) and (C) are present in a ratio by weight of A to B to C of 1:(0.31–1.5):(0.31–1.5).

Flowable or pumpable emulsion concentrates are those which have a viscosity at 20° C. below 20 Pa·s, as measured with a Brookfield rotational viscosimeter (type RVF, spindle TE, 4 r.p.m.).

Suitable water-insoluble oil components are any fatty compounds liquid at 20° C. or mixtures thereof, including mixtures of liquid and solid fatty compounds or paraffins dissolved therein providing the mixtures are liquid at 20° C. or have a viscosity at 20° C. below 20 Pa·s.

Suitable liquid oil components are, above all, hydrocarbons and fatty acid esters liquid at room temperature. Liquid hydrocarbons are, for example, paraffin oils, liquid polyolefins or alkyl cyclohexanes, for example 1,3-diisooctyl cyclohexane. Suitable liquid fatty acid esters are, for example, the methyl and isopropyl esters of fatty acids containing 12 to 22 carbon atoms, for example methyl laurate, methyl stearate, methyl oleate, methyl erucate, isopropyl palmitate, isopropyl stearate, isopropyl oleate. Other suitable oil components are n-butyl stearate, n-hexyl laurate, n-decyl oleate, isooctyl stearate, isononyl palmitate, isononyl isononanoate, 2-ethylhexyl palmitate, 2-ethylhexyl laurate, 2-hexyldecyl stearate, 2-octyl dodecyl palmitate, oleyl oleate, oleyl erucate, erucyl oleate and esters obtainable from technical aliphatic alcohol mixtures and technical aliphatic carboxylic acids, for example esters of saturated and unsaturated fatty alcohols containing 12 to 22 carbon atoms and saturated and unsaturated fatty acids containing 12 to 22 carbon atoms which are obtainable from animal and vegetable fats. Naturally occurring liquid wax esters as present in sperm oil and jojoba oil are also suitable.

Suitable liquid dicarboxylic acid esters are, for example, di-n-butyl adipate, di-n-butyl sebacate, di-(2-ethylhexyl)-adipate, di-(2-ethylhexyl)-succinate, diisotridecyl azelate. Suitable diol esters are, for example, ethylene glycol dioleate, ethylene glycol diisotridecanoate, propylene glycol di-(2-ethylhexanoate), butanediol diisostearate or neopentyl glycol dicaprylate.

Liquid triglycerides such as, for example, olive, oil, sunflower oil, soybean oil, peanut oil, rapeseed oil, almond oil, palm oil or the liquid fractions of coconut oil or palm oil and also animal oils, for example neat's foot oil, the liquid fractions of beef tallow, or even synthetic triglyceride oils obtainable, for example, by esterification of glycerol with caprylic acid/capric acid mixtures, technical oleic acid or palmitic acid/oleic acid mixtures may also be used as oil components.

Preferred oil components (A) are the hydrocarbons, dialkyl ethers and fatty acid esters liquid at 20° C. which contain 16 to 36 carbon atoms or mixtures of these components.

Preferred hydrophilic nonionic emulsifiers (B) are adducts of ethylene oxide with linear fatty alcohols, fatty acids, fatty acid partial glycerides, sorbitan fatty acid esters or alkyl (oligo)glycosides with an HLB value of 11 to 19. The HLB value is the value corresponding to formula I:

$$HLB = \frac{100 - L}{5} \qquad (I)$$

in which L is the percentage (in % by weight) of the lipophilic alkyl or acyl groups in the ethylene oxide adducts. Particularly suitable hydrophilic nonionic emulsifiers are the adducts of 8 to 30 moles of ethylene oxide with linear fatty alcohols containing 12 to 22 carbon atoms.

The lipophilic co-emulsifiers (C) are nonionic polar lipids containing one or more hydroxyl groups which are insoluble or only dispersible in water and which, on account of their low hydrophilicity, are not suitable on their own for the production of oil-in-water emulsions.

According to the invention, suitable co-emulsifiers are saturated fatty alcohols containing 16 to 22 carbon atoms, for example cetyl alcohol, stearyl alcohol, arachidyl alcohol or behenyl alcohol or mixtures of these alcohols which are obtained in the industrial hydrogenation of vegetable and animal fatty acids containing 16 to 22 carbon atoms or the corresponding fatty acid methyl esters. Other suitable co-emulsifiers are partial esters of a polyol containing 3 to 6 carbon atoms and saturated fatty acids containing 14 to 22 carbon atoms. Corresponding partial esters are, for example, the monoglycerides of palmitic and/or stearic acid, the sorbitan monoesters and/or diesters of myristic acid, palmitic acid, stearic acid or mixtures of these fatty acids, the monoesters of trimethylol propane, erythritol or pentaerythritol and saturated fatty acids containing 14 to 22 carbon atoms. Monoesters are also understood to include the technical monoesters which are obtained by esterification of 1 mole of polyol with 1 mole of fatty acid and which represent a mixture of monoester, diester and unesterified polyol. Saturated fatty alcohols containing 16 to 22 carbon atoms or partial esters of polyols containing 3 to 6 carbon atoms and fatty acids containing 14 to 22 carbon atoms are particularly suitable.

The emulsion concentrates according to the invention are preferably produced by the process described in DE 38 191 193. Accordingly, the oil component (A), the hydrophilic emulsifier (B) and the lipophilic co-emulsifier (C) are preferably selected so that the emulsions produced with them have a phase inversion temperature below 100° C. The emulsifiers (B) and co-emulsifiers (C) are mixed with the oil component (A) and heated to the phase inversion temperature. Water with substantially the same temperature is then added with stirring or, conversely, the mixture of oil component, emulsifier and co-emulsifier is stirred into the water heated to the phase inversion temperature. Alternatively, emulsification may also be carried out below the phase inversion temperature and the emulsion subsequently brought briefly into the phase inversion temperature range by heating. A very fine-particle emulsion concentrate still flowable at 20° C. is obtained after cooling.

The emulsion concentrate according to the invention is particularly suitable for the production of cosmetic and pharmaceutical oil-in-water emulsions. Either the continuous aqueous phase or the disperse oil phase or both may be incorporated in the emulsion concentrate without any further application of heat.

The aqueous phase with which the emulsion concentrate is diluted may contain any water-soluble ingredients, for example water-soluble cosmetic agents, water-soluble proteins or protein degradation products, preservatives, dyes, fragrances, propylene glycol or glycerol, magnesium salts or other typical water-soluble components in dissolved form. The aqueous continuous phase preferably contains a water-soluble, natural or synthetic polymer which improves the cosmetic properties of the emulsions by increasing their viscosity. A particularly effective combination of hydrocolloids for improving the cosmetic properties of such emulsions is a mixture of nonionic cellulose ethers, for example hydroxypropyl cellulose, and crosslinked acrylic acid polymers which are commercially obtainable, for example, under the name of Carbopol® (cf. DE 35 21 713 A1).

However, an oil liquid at normal temperature or a liquid mixture of oils and fatty components is preferably used as the oil phase. Accordingly, a preferred embodiment of the invention is a process for the production of oil-in-water emulsions in which the emulsion concentrate according to the invention is mixed with an oil component liquid at 20° C. in the absence of heat and the resulting mixture is diluted with water or an aqueous solution of a water-soluble polymer.

The emulsion concentrates according to the invention are fine-particle concentrates with very high stability in storage so that they are particularly suitable for use as a preformed emulsion component which, by virtue of its flow properties, is eminently suitable for storage and for transport to a minimally equipped processing station where useful cosmetic and pharmaceutical oil-in-water emulsions can be prepared with the simplest of means.

The following Examples are intended to illustrate the invention:

| 1. Emulsion concentrate | Examples | | | | |
|---|---|---|---|---|---|
| | 1 | 2 | 3 | C1 | C2 |
| 2-Ethylhexyl stearate | 20 | 10 | — | 20 | 20 |
| Cetyl/stearyl isononanoate | — | — | 20 | — | — |
| Cetyl palmitate | — | — | 0.8 | — | — |
| Cetyl/stearyl alcohol + 12 moles EO | 7.5 | 1.8 | 0.8 | 5.6 | 4.0 |
| Cetyl/stearyl alcohol + 20 moles EO | — | 7.6 | 9.0 | — | — |
| Cetyl/stearyl alcohol (50:50) | 10 | 1.8 | 7.8 | 7.8 | 6.0 |
| Glycerol mono/distearate | — | 9.1 | 3.8 | — | — |
| Water | 62.5 | 69.7 | 57.8 | 66.6 | 70 |
| Viscosity (23° C.) Pa · s (Brookfield RVF, spindle TE, 4 r.p.m. | 4 | 1.6 | 1.2 | 237 | 62 |

1.2 Production

The hydrophilic emulsifiers and lipophilic emulsifiers are heated with the oil component to the phase inversion temperature (in this case 85° C). Water with the same temperature (85° C.) was then added, followed by intensive mixing. A fine-particle emulsion was obtained after cooling to 20° C. Viscosity was measured with a rotational viscosimeter 5 hours after preparation of the dispersion.

In the comparison formulation C, the ratio by weight of oil (A) to emulsifier (B) to co-emulsifier (C) is 1:0.28:0.39. Despite this only slight deviation from the quantity ratio according to the invention, the emulsion is no longer free-flowing.

2. Application Example
2.1 Formulation

| | |
|---|---|
| Emulsion concentrate according to Example 1 | 20% by weight |
| Paraffin oil | 2% by weight |
| Caprylic/capric acid triglyceride | 4% by weight |
| Crosslinked polyacrylic acid (2% dispersion) | 20% by weight |
| Sodium hydroxide (1% in water) | 10% by weight |
| Glycerol (86%) | 5% by weight |
| Water | 39% by weight |

2.2 Production

The oil components were mixed with the emulsion concentrate at 20° C. and emulsified while stirring. The swollen polymer (polyacrylic acid dispersion, NaOH), glycerol and water were then incorporated.

We claim:

1. An aqueous emulsion concentrate consisting of:
A) a water-insoluble oil component consisting of at least one of a hydrocarbon, a dialkyl ether liquid at 20° C., and a fatty acid ester of a fatty alcohol, wherein the ester contains from 16 to 36 carbon atoms and is liquid at 20° C.;
B) a hydrophilic nonionic emulsifier consisting of at least one adduct of ethylene oxide with (a) a linear fatty alcohol, (b) a fatty acid, (c) a fatty acid partial glyceride, (d) a sorbitan fatty acid ester, or (e) an alkyl glycoside, wherein the at least one adduct has an HLB value of from about 11 to about 19;
C) a lipophilic co-emulsifier consisting of at least one of (i) a saturated fatty alcohol containing 16 to 22 carbon atoms, or (ii) a partial ester of a polyol containing 3 to 6 carbon atoms and a fatty acid containing 14 to 22 carbon atoms; and
D) from about 50 to about 70% by weight of water, based on the weight of the concentrate;
wherein components A), B) and C) are present in a ratio by weight of A:B:C of 1:(0.31–1.5):(0.31–1.5); and wherein the emulsion concentrate is flowable and pumpable at 20° C.

2. A process for the production of an oil-in-water emulsion comprising the steps of (I) mixing an aqueous emulsion concentrate consisting of
   A) a water-insoluble oil component consisting of at least one of a hydrocarbon, a dialkyl ether liquid at 20° C., and a fatty acid ester of a fatty alcohol, wherein the ester contains from 16 to 36 carbon atoms and is liquid at 20° C.;
   B) a hydrophilic nonionic emulsifier consisting of at least one adduct of ethylene oxide with (a) a linear fatty alcohol, (b) a fatty acid, (c) a fatty acid partial glyceride, (d) a sorbitan fatty acid ester, or (e) an alkyl glycoside, wherein the at least one adduct has an HLB value of from about 11 to about 19;
   C) a lipophilic co-emulsifier consisting of at least one of (i) a saturated fatty alcohol containing 16 to 22 carbon atoms, or (ii) a partial ester of a polyol containing 3 to 6 carbon atoms and a fatty acid containing 14 to 22 carbon atoms; and
   D) from about 50 to about 70% by weight of water, based on the weight of the concentrate;
   wherein components A), B) and C) are present in a ratio by weight of A:B:C of 1:(0.31–1.5):(0.31–1.5) ; and wherein the emulsion concentrate is flowable and pumpable at 20° C.
with an oil component liquid at 20° C. without the application of heat; and (II) diluting the resulting mixture with water or an aqueous solution of a water-soluble polymer or both.

3. The process of claim 2 wherein in step II said water-soluble polymer in said aqueous solution is a mixture of a nonionic cellulose ether and a crosslinked acrylic polymer.

* * * * *